United States Patent [19]

Saino et al.

[11] Patent Number: 5,061,787
[45] Date of Patent: Oct. 29, 1991

[54] NOVEL SPERGUALIN-RELATED COMPOUNDS AND COMPOSITIONS

[75] Inventors: Tetsushi Saino, Yono; Tsugio Tomiyoshi; Kyuichi Nemoto, both of Tokyo; Yoshihisa Umeda, Otsu, all of Japan

[73] Assignees: Nippon Kayaku Kabushiki Kaisha, Tokyo; Takara Shuzo Kabushiki Kaisha, Kyoto, both of Japan

[21] Appl. No.: 363,538

[22] Filed: Jun. 8, 1989

[30] Foreign Application Priority Data

Jun. 24, 1988 [JP] Japan ............................ 63-154590

[51] Int. Cl.$^5$ ..................... C07C 237/00; A61K 37/02
[52] U.S. Cl. .................................. 530/331; 530/323; 564/158; 564/159; 514/885
[58] Field of Search ................ 564/154, 158; 530/323, 530/331; 514/885

[56] References Cited

U.S. PATENT DOCUMENTS 4,518,532  5/1985  Umezawa et al. ................ 564/159
4,525,299  6/1985  Umezawa et al. ................ 564/159

OTHER PUBLICATIONS

Peptide Chemistry, "Spergualin Analogues: Syntheses and Their Biological Activities", 1987, pp. 671–674.
Nishizawa et al, Jol. of Antibiotics, vol. 41, No. 11, 1988, pp. 1629–1643 "Synthesis and Biological Activity of Spergualin Analogues I".

Primary Examiner—C. Warren Ivy
Assistant Examiner—Raymond Covington
Attorney, Agent, or Firm—Nields & Lamack

[57] ABSTRACT

The present invention relates to novel spergualin-related compounds represented by the general formula [I]:

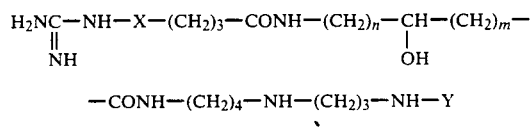

—CONH—(CH$_2$)$_4$—NH—(CH$_2$)$_3$—NH—Y wherein X is —(CH$_2$)$_{1\sim 5}$ or

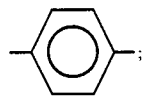

Y is a hydrogen atom or a residue obtained by removing a hydroxyl group from the carboxyl group of an amino acid or a peptide; m is 0, 1 or 2 and n is 1 or 2, with the proviso that Y is not a hydrogen atom when n is 2 and m is 0.

This compounds are stable and exhibit a high immunosuppressive activity.

6 Claims, No Drawings

NOVEL SPERGUALIN-RELATED COMPOUNDS AND COMPOSITIONS

BACKGROUND OF THE INVENTION

Spergualin is an antibiotic produced by microorganisms belonging to the genus Bacillus and many related compounds thereof have been synthesized.

Among the spergualin and its related compounds which have been already known, highly active compounds are poor in chemical stability, while chemically stable compounds are poor in activity. Therefore, it is expected to develop spergualin-related compounds which are chemically stable and highly active and yet has a low toxicity.

SUMMARY OF THE INVENTION

The inventors of the present invention have extensively studied and have found that a compound represented by the general formula [I]:

$$H_2NC-NH-X-(CH_2)_3-CONH-(CH_2)_n-CH-(CH_2)_m-$$
$$\underset{NH}{\|} \qquad \qquad \qquad \qquad \underset{OH}{|}$$

$$-CONH-(CH_2)_4-NH-(CH_2)_3-NH-Y$$

wherein X is $-(CH_2)_{1-5}$ or

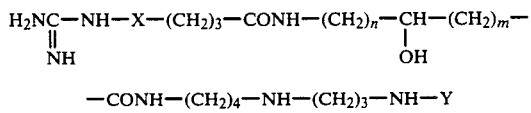

Y is a hydrogen atom or a residue obtained by removing a hydroxyl group from the carboxyl group of an amino acid or a peptide; m is 0, 1 or 2 and n is 1 or 2, with the proviso that Y is not a hydrogen atom when n is 2 and m is 0, is stable and exhibits a high immunosuppressive activity. The present invention has been accomplished on the basis of this finding.

DETAILED DESCRIPTION OF THE INVENTION

In the general formula [I], the group Y is a hydrogen atom or a residue obtained by removing a hydroxyl group from the carboxyl group of an amino acid or a peptide. Examples of the amino acid and the peptide include the following compounds, the configuration of which may be of S,R type or R,S type except glycine, β-alanine and γ-aminobutyric acid:

(1) amino acids alanine, arginine, ornithine, aspartic acid, asparagine, cysteine, cystine, glutamic acid, glutamine, pyroglutamic acid, glycine, histidine, lysine, proline, hydroxyproline, isoleucine, leucine, methionine, phenylalanine, phenyl-substituted phenylalanine, serine, threonine, tryptophan, homoserine, tyrosine, valine, phenylglycine, p-hydroxyphenylglycine, 4-hydroxymethyl-3-hydroxyphenylglycine, β-alanine, γ-aminobutyric acid and 3-amino2-hydroxy-4-phenylbutyric acid.

(2) peptides

Di- or tri-peptides obtained by the condensation of one or more of the above amino acids are preferable. Examples of the peptide include alanylalanine, leucylleucine, valylvaline, phenylalanylphenylalanine, tyrosyltyrosine, phenylglycylphenylglycine, glycylglycine, isoleucylisoleucine, leucylphenylalanine, phenylalanylleucine, leucylphenylglycine, phenylglycylleucine, glycylglycylglycine, phenylglycylphenylglycylphenylglycine, phenylalanylphenylalanylphenylalanine and leucylleucylleucine.

Preferred examples of the amino acid and the peptide include phenylglycine, phenylalanine, leucine, aspartic acid, tryptophan, alanine and di- or tripeptides of them, among which phenylglycine tyrosine and leucylleucine are more preferred.

Each of the novel spergualin-related compounds represented by the general formula [I] forms a salt together with an acid. The acid may be any organic or inorganic acid, as far as it is non-toxic. Although the inorganic acid is not particularly limited, preferred examples thereof include hydrochloric, sulfuric, nitric and phosphoric acids. Preferred examples of the organic acid include acetic, propionic, succinic, fumaric, maleic, malic, tartaric, glutaric, citric, benzenesulfonic, toluenesulfonic, methanesulfonic, ethanesulfonic, propanesulfonic, aspartic and glutamic acids, though the organic acid is not particularly limited.

Representative examples of the compound represented by the general formula [I] are shown in Table 1.

TABLE 1

$$H_2N-C-NH-X-(CH_2)_3-CONH-(CH_2)_n-CH+CH_2)_m-$$
$$\underset{NH}{\|} \qquad \qquad \qquad \qquad \underset{OH}{|}$$

$$-CO-NH-(CH_2)_4-NH-(CH_2)_3-NH-Y$$

| No. of compound | X | n | m | Configuration of hydroxyl group | Y |
|---|---|---|---|---|---|
| 1 | $-(CH_2)_3-$ | 1 | 1 | S, R or RS | H |
| 2 | " | " | " | " | ph G |
| 3 | " | " | " | " | Leu—Leu |
| 4 | $-CH_2-$ | " | " | " | H |
| 5 | " | " | " | " | ph G |
| 6 | " | " | " | " | Leu—Leu |
| 7 | $-(CH_2)_2-$ | " | " | " | H |
| 8 | " | " | " | " | ph G |
| 9 | " | " | " | " | Leu—Leu |
| 10 | $-(CH_2)_4-$ | " | " | " | H |
| 11 | " | " | " | " | ph G |
| 12 | $-(CH_2)_4-$ | 1 | 1 | S, R or RS | Leu—Leu |
| 13 | $-(CH_2)_5-$ | " | " | " | H |
| 14 | " | " | " | " | ph G |
| 15 | " | " | " | " | Leu—Leu |
| 16 | 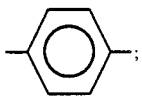 | " | " | " | H |
| 17 | " | " | " | " | ph G |
| 18 | " | " | " | " | Leu—Leu |
| 19 | $-(CH_2)_2-$ | 1 | 0 | " | H |
| 20 | " | " | " | " | ph G |
| 21 | " | " | " | " | Leu—Leu |
| 22 | $-(CH_2)_3-$ | " | " | " | H |
| 23 | " | " | " | " | ph G |
| 24 | " | " | " | " | Leu—Leu |
| 25 | $-(CH_2)_4-$ | 1 | 0 | S, R or RS | H |
| 26 | " | " | " | " | ph G |
| 27 | " | " | " | " | Leu—Leu |
| 28 | 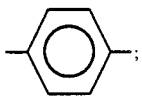 | " | " | " | H |
| 29 | " | " | " | " | ph G |
| 30 | " | " | " | " | Leu—Leu |

TABLE 1-continued $$H_2N-\underset{\underset{NH}{\|}}{C}-NH-X-(CH_2)_3-CONH-(CH_2)_n-\underset{\underset{OH}{|}}{CH}(CH_2)_m-$$

$$-CO-NH-(CH_2)_4-NH-(CH_2)_3-NH-Y$$

| No. of compound | X | n | m | Configuration of hydroxyl group | Y |
|---|---|---|---|---|---|
| 31 | —(CH$_2$)$_3$— | 2 | 0 | " | ph G |
| 33 | " | 2 | 0 | " | Leu—Leu |
| 34 | 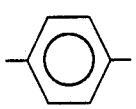 | 2 | 0 | " | ph G |
| 34 | 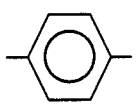 | 2 | 0 | " | H |
| 36 | " | 2 | 0 | " | Leu—Leu |

In Table 1, phG refers to

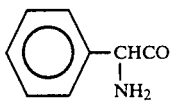—CHCO
         |
         NH$_2$ and LeuLeu refers to $$(CH_3)_2-CH-CH_2\underset{\underset{NH_2}{|}}{CH}-CON\underset{\underset{CO-}{|}}{H}CH-CH_2-CH-(CH_3)_2.$$

The compound represented by general formula [I] can be prepared by removing protective groups from a protected compound represented by the general formula [II]:

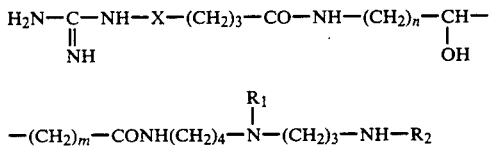

wherein X is -(CH$_2$)$_{\overline{1-5}}$ or

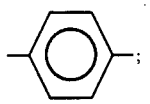;

R$_1$ is an amino-protective group; R$_2$ is an amino-protective group or a residue obtained by removing a hydroxyl group from the carboxyl group of an amino acid or peptide having a protected amino group (the side chain of the residue may be protected); m is 0, 1 or 2 and n is 1 or 2, with the proviso that Y is not a hydrogen atom when n is 2 and m is 0.

The removal of the protective group may be carried out by reduction, acidolysis, hydrolysis or the like.

The removal is generally carried out in an inert solvent at a temperature of from −60° C. to the boiling point of the solvent, preferably at a temperature of about −50° to 100° C. The inert solvent may be water or a hydrophilic organic solvent and examples of the solvent include lower alcohols such as methanol and ethanol; ketones such as acetone and methyl ethyl ketone; amides such as dimethylformamide and dimethylacetamide; cyclic ethers such as tetrahydrofuran and dioxane; lower aliphatic acids such as acetic and trifluoroacetic acids; liquid ammonia and liquid hydrogen fluoride.

The spergualin-related compound represented by the general formula [I] can be isolated from the reaction mixture of the above removal step as follows. When, for example, the removal is carried out by catalytic reduction with palladium black, after the removal of the catalyst from the reaction mixture by filtration, the filtrate is concentrated under a reduced pressure and the residue is purified by an ordinary method using CM-Sephadex ® (Na$^+$) or Sephadex ® LH-20 (see T. Takeuchi et al., J. Antibiotics, 34, 1619 (1981)). Alternately, when the removal is carried out by the use of trifluoroacetic acid, the reaction mixture is concentrated under a reduced pressure and the residue is purified by an ordinary method as described above.

According to the isolation method as described above, the spergualin-related compound represented by the general formula [I] is obtained as a hydrochloride. The conversion of the hydrochloride into another salt may be carried out by dissolving the hydrochloride in water, passing the obtained aqueous solution through a strongly basic ion exchange resin to collect fractions containing an objective compound, neutralizing the fractions by the addition of an objective acid or a solution thereof in water or a hydrophilic organic solvent such as methanol, ethanol, acetone, tetrahydrofuran or dioxane and evaporating the neutralized solution under a reduced pressure to dryness. Alternatively, when the neutralized solution contains an organic solvent, the neutralized solution is distilled under a reduced pressure to remove the solvent and the residue is freeze-dried to obtain an objective salt. Further, the conversion may be carried out by adding silver hydroxide or an aqueous solution of silver oxide to the hydrochloride of the compound of the general formula [I] to thereby neutralize the hydrochloric acid, filtering out insoluble silver chloride, adding an objective acid to the filtrate to form an objective salt and freeze-drying it.

The objective salt prepared above is sometimes present as a hydrate depending upon the treatment conditions.

The protected spergualin-related compound represented by the general formula [II] to be used as a raw material in the present invention can be prepared as follows:

(a) a compound represented by the general formula [II] wherein R$_1$ and R$_2$ are each an amino-protective group can be prepared according to the process disclosed in EP-A-105193 by reacting a di-protected spermidine represented by the general formula [III]:

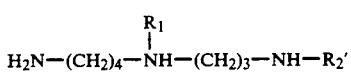

wherein R$_1$ and R$_2'$ are each an amino-protective group, with a reactive derivative of a protected amino acid represented by the general formula [IV]:

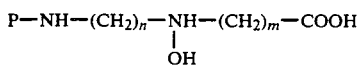

wherein P is an amino-protective group different from $R_1$ or $R_2'$ and n and m are as defined above, to obtain a compound represented by the general formula:

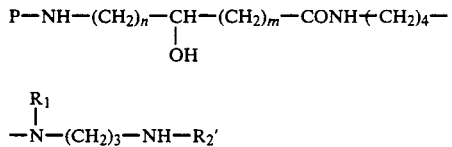

wherein P, $R_1$ and $R_2'$ are each as defined above, freeing the compound of the amino-protective group P and reacting the resulting compound with a reactive derivative of an ω-guanidino fatty acid represented by the general formula [V]:

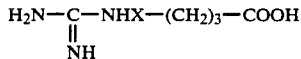

wherein X is as defined above,
or
(b) a compound represented by the general formula [II] wherein $R_2$ is a residue obtained by removing a hydroxyl group from the carboxyl group of an amino acid or peptide having a protected amino group (the side chain of the residue may be protected) can be prepared by reacting a compound represented by the formula [I] wherein Y is a hydrogen atom with a reactive derivative of a protected amino acid or peptide represented by the general formula [VI]:

Y-OH wherein Y is as described above.

The condensation in the above processes (a) and (b) may be carried out by any method which has been ordinarily used for the preparation of a peptide. Examples of the method include the carbodiimide method using dicyclohexylcarbodiimide or 1-ethyl-3-(3-dimethylaminopropyl)-carbodiimide; the azide method using a hydrazide; the mixed anhydride method using ethyl chlorocarbonate or isobutyl chlorocarbonate; the active easter method using cyanomethyl ester, vinyl ester, substituted or unsubstituted phenyl ester, thiophenyl ester or hydroxysuccinimide ester; the O-acylhydroxyamine derivative method using acetoxime or cyclohexanone oxime; the N-acyl compound method using carbonyldiimidazole; and the carboxylic acid activation method using 1,3-thiazolidine-2thione. The solvent to be used in the condensation may be any one which is ordinarily used in the formation of a peptide. Examples thereof include ethers such as diethyl ether, tetrahydrofuran and dioxane; esters such as ethyl acetate; ketones such as acetone and methyl ethyl ketone; halogenated hydrocarbons such as methylene chloride and chloroform; amides such as dimethylformamide and dimethylacetamide; and nitriles such as acetonitrile. These solvents may be each used alone or as a mixture thereof with water if it is miscible with water.

The amino-protective group to be used in the present invention includes a benzyloxycarbonyl group, substituted benzyloxycarbonyl groups, such as a p-methoxybenzyloxycarbonyl group, and t-butyloxycarbonyl, t-amyloxycarbonyl, formyl, trityl and o-nitrophenylsulfenyl groups.

The protective group for the carboxyl group of the amino acid side chain includes lower alkyl, t-butyl, benzyl and substituted benzyl groups; the one for the hydroxyl group thereof includes t-butyl and benzyl groups; the one for the mercapto group includes benzyl and p-methoxybenzyl groups; the one for the imidazole group includes benzyloxycarbonyl, benzyl and tosyl groups and the one for the guanidine group includes nitro, tosyl and t-butyloxycarbonyl groups, though they are each not always limited to the above groups.

The compounds of the present invention as prepared above may be formulated into a drug for oral or parenteral administration according to an ordinary method, if necessary, by the use of a suitable carrier.

When the drug is an injection, it is preferred that the content of an active ingredient therein be generally 0.1 to 30% by weight, still preferably 1 to 10% by weight.

When the drug is one for oral administration, it may be in the form of tablet, capsule, powder, granule or dry syrup. The content of an active ingredient in the capsule, granule or powder is generally 5 to 100% by weight, preferably 25 to 100% by weight.

Although the dose varies depending upon the age, weight and symptom of a patient and the object of treatment, it is 1 to 100 mg/kg.day in parenteral administration, while it is 5 to 1000 mg/kg.day in oral administration.

Effect

1 Stability of the compound of the invention in water (1) Method of experiment

A compound of the present invention was dissolved in water to obtain a 0.5 w/w % aqueous solution. This aqueous solution was kept at 40±1° C., sampled at intervals of a determined time and subjected to high-performance liquid chromatography to determine the peak area ratio. The residual rate was calculated on the basis of this ratio.

(2) Results of experiment

The residual rates of the compounds after the lapse of a predetermined time are shown in Table 2 by assuming the residual rate at the start of the experiment to be 100%.

TABLE 2

Residual rate of the compound of the invention in 0.5% aqueous solution (%)

| No. of compound | Hours | | | | | |
|---|---|---|---|---|---|---|
| | 0 | 24 | 48 | 72 | 96 | 168 |
| 1 | 100 | 99.76 | 101.21 | 99.98 | 99.22 | 99.05 |
| 4 | " | 102.50 | 99.38 | 99.05 | 101.10 | 99.23 |
| 16 | " | 93.08 | 101.12 | 99.01 | 98.15 | 100.91 |
| 19 | " | 99.38 | 99.05 | 101.20 | 99.03 | 99.86 |
| 22 | " | 100.05 | 101.23 | 98.09 | 99.87 | 98.07 |
| 25 | " | 98.19 | 99.33 | 101.56 | 99.48 | 99.15 |
| 28 | " | 99.12 | 100.87 | 99.46 | 98.92 | 99.08 |

As shown in Table 2, the compounds of the present invention are substantially stable even after the lapse of one week.

Activity

The physiological activity of the compound according to the present invention will now be experimentally illustrated.

1. Method of experiment (a) A skin piece (5×10 mm) of the tail of a male WKAH (RT1$^k$) rat (of 7 to 10 weeks of age) was transplanted to the back of a male F 344 (RT1$^{1v1}$) rat (of 7 to 10 weeks of age) to carry out the rat skin transplantation test.

A compound of the present invention was intraperitoneally administered to the latter rat to determine the immunosuppressive effect thereof. The effect is shown by the survival times of allografts. In this experiment, a known compound represented by the general formula (I) wherein X is -(CH$_2$)$_3$-, n is 2, m is 0 and Y is H was used as a control (b) The results of the rat skin transplantation test are shown in Table 3.

TABLE 3

| | Mean survival time (days) Dose (mg/kg) | | | |
|---|---|---|---|---|
| | 0 | 3.0 | 6.0 | 12.0 |
| Control n = 2, m = 0, Y = H | 7.0 ± 0.6 | 7.6 ± 1.1 | 8.5 ± 0.7 | 9.3 ± 2.5 |
| Compound 1 (S-type) | 6.9 ± 0.7 | 7.7 ± 0.8 | 10.3 ± 1.0 | 14.5 ± 0.8 |
| Compound 13 (S-type) | — | 9.6 ± 0.5 | 17.0 ± 4.0 | — |
| (RS-type) | 6.4 ± 0.5 | 8.5 ± 0.6 | 14.0 ± 2.8 | — |

EXAMPLE

10-{N-(7-Guanidinoheptanoyl)-γ-amino-β-(S)hydroxybutyryl}-1,5,10-triazadecane trihydrochloride (Compound 1)

6.7 g (9.3 mmol) of 10-{N-(7-guanidinoheptanoyl)-γ-amino-β-(S)-hydroxybutyryl}-1,5-dibenzyloxycarbonyl-1,5,10-triazadecane hydrochloride was dissolved in 60 ml of methanol, followed by the addition of 1.3 g of acetic acid and 0.9 g of palladium black. The catalytic reduction was carried out at a room temperature under normal pressure for 4 hours.

The reaction mixture was filtered to remove the catalyst and the filtrate was concentrated under reduced pressure to give 5.9 g of an oil (the yield was quantitative). This oil was dissolved in 60 ml of distilled water, placed on a column packed with 500 ml of Sephadex ® C-25 (Na+) and subjected to gradient elution between 2500 ml of distilled water and 2500 ml of a 1.0 M aqueous solution of sodium chloride to collect fractions containing an objective compound. The fractions were combined and dryed under reduced pressure, followed by the addition of methanol. The obtained mixture was filtered to remove an insoluble sodium chloride. The isolation of the objective compound from the obtained oil was carried out as follows. In order to remove a trace amount of sodium chloride remaining in the oil, the oil was dissolved in 20 ml of methanol, placed on a column packed with 300 ml of Sephadex ® LH-20 and eluted with methanol to obtain fractions containing the objective compound. The fractions were combined and concentrated under reduced pressure to obtain an oil. This oil was dissolved in 35 ml of distilled water and filtered to remove an insoluble material. The filtrate was freeze-dried to give 3.77 g of the title compound (yield: 55.9%).

NMR(D$_2$O, external TMS) δ=1.5~3.1 (m, 18H), 3.2~4.1 (m, 12H), 4.4~4.8 (m, H)

IR(KBr) ν(cm$^{-1}$)=3320, 2930, 1640, 1545, 1460, 1365, 1170, 1080 [α]$_D^{20}$+2.9° (C=1.02, H$_2$O)

Referential Example

Synthesis of 10-{N-(7-guanidinoheptanoyl)-γ-amino-β-(S)-hydroxybutyryl}-1,5-dibenzyloxycarbonyl-1,5,10-triazadecane hydrochloride (1) 10-(γ-N-tert-butyloxycarbonyl-β-(S)-hydroxybutyryl)-1,5-dibenzyloxycarbonyl-1,5,10-triazadecane 2.63 g (12.0 mmol) of γ-N-tert-butyloxycarbonylβ-(S)-hydroxybutyric acid and 2.76 g (18.0 mmol) of N-hydroxybenzotriazole were dissolved in a mixture of 50 ml of dichloromethane and 30 ml of tetrahydrofuran. The obtained solution was cooled with ice, followed by the addition of 3.96 g (18.0 mmol) of dicyclohexylcarbodiimide. The obtained mixture was reacted under cooling with ice for 15 minutes. A solution of 5.4 g (14.4 mmol) of 1,5-dibenzyloxycarbonyl-1,5,10-triazadecane hydrochloride and 1.6 g (15.8 mmol) of triethylamine in dichloromethane was added to the reaction mixture obtained above under cooling with ice to carry out the reaction at a room temperature overnight. The reaction mixture was filtered to remove a precipitate and the filtrate was concentrated under reduced pressure. The obtained oily residue was dissolved in 200 ml of ethyl acetate and washed with distilled water twice. The organic layer was dried over anhydrous sodium sulfate and filtered to remove the drying agent. The filtrate was concentrated under reduced pressure to give 11.0 g of a pale yellow oil.

This oil was placed on a column placed with Silica gel ® 60 (mfd. by Merck & Co.) and eluted with chloroform and a chloroform/methanol (20:1 v/v) mixture successively to give 7.0 g of an oil (yield: 94.85%).

NMR (CD$_3$OD) δ=0.9~2.0 (m, 15H), 14.2 (s, 9H), 2.1~2.5 (d, 2H, J=5Hz), 2.6~9.0 (b, 4H), 2.8~3.5 (m, 10H), 3.7~4.3 (m, H), 5.03 (s, 2H), 5.07 (s, 2H), 7.28 (s, 10H).

TLC (chloroform:methanol=10:1, v/v) Rf=0.42

(2) 10-(γ-amino-β-(S)-hydroxybutyryl)-1,5-dibenzyloxycarbonyl-1,5,10-triazadecane hydrochloride 7.0 g (11.38 mmol) of 10-(γ-N-tert-butyloxycarbonyl-β-(S)-hydroxybutyryl)-1,5-dibenzyloxycarbonyl1,5,10-triazadecane was dissolved in 10 ml of dichloromethane to give a solution. 10 ml of a 4N solution of hydrochloric acid in dioxane was added to the solution under cooling with ice to carry out the reaction at a room temperature for 3 hours.

The reaction mixture was concentrated under reduced pressure to give an oil. This oil was washed with 100 ml of n-hexane and concentrated under reduced pressure to give 6.3 g of an oil (the yield was guantitative).

TLC (chloroform:methanol:17% aqueous ammonia=6:2.5:0.5 v/v) Rf=0.48

(3) 10-{N-(7-guanidinoheptanoyl)-γ-amino-β-(S)hydroxybutyryl}-1,5-dibenzyloxycarbonyl-1,5,10-triazadecane hydrochloride 2.92 g (13.05 mmol) of 7-guanidinoheptanoic acid hydrochloride was dissolved in 30 ml of dimethylformamide to give a solution. 1.8 g (15.64 mmol) of N-hydroxysuccinimide and 3.23 g (15.64 mmol) of N,N'-dicyclohexylcarbodiimide were added to the solution under cooling with ice to carry out the reaction at a room temperature overnight. The precipitate was filtered off and the filtrate was used as such in the following step.

6.3 g (11.38 mmol) of oily 10-(γ-amino-β-(S)-hydroxybutyryl)1,5-dibenzyloxycarbonyl-1,5,10-triazadecane hydrochloride was dissolved in 40 ml of dimethylformamide to give a solution. 1.38 g (13.66 mmol) of triethylamine was added to the solution under cooling with ice, followed by the addition of the above solution of an ester of 7-guanidinoheptanoic acid hydrochloride with N-hydroxysuccinimide in dimethylformamide. The obtained mixture was reacted at a room temperature overnight and concentrated under reduced pressure to obtain an oily residue. This residue was washed with 100 ml of n-hexane twice and concentrated under reduced pressure to obtain a residue. 150 ml of distilled water was added to the residue. The mixture was filtered to remove an insoluble material and the filtrate was concentrated under reduced pressure to give 14.5 g of an oil.

This oil was column-chromatographed over Silica gel 60 mfd. by Merck & Co.) and developed with a chloroform/methanol/17% aqueous ammonia (6:2.5:0.5 v/v) mixture to give 6.7 g of an oil (yield: 81.7%).

NMR (CD$_3$OD) δ=0.9~2.0 (M, 12H), 2.0~2.5 (m, 4H), 2.6~3.5 (m, 12H), 3.5~9.0 (b, 9H), 3.6~4.2 (m, H), 5.03 (s, 2H), 5.07 (s, 2H), 7.27 (s, 10H).

IR(KBr) ν(cm$^{-1}$)=3290, 2930, 1640, 1535, 1420, 1360, 1245, 1135, 1075, 1015.

TLC (chloroform:methanol:17% aqueous ammonia=6:2.5:0.5 v/v) Rf=0.48.

| No. of compound | 10-{N-(5-Guanidinopentanoyl)-γ-amino-α-hydroxybutyryl}-1,5-dibenzyloxycarbonyl-1,5-10-triazadecane hydrochloride | 10-{N-(5-Guanidinopentanoyl)-γ-amino-α-hydroxybutyryl}-1,5,10-triazadecane trihydrochloride |
|---|---|---|
| 4 | NMR (CD$_3$OD) δ = 0.9~2.5 (m, 14H), 2.6~3.6 (m, 12H), 3.8~4.2 (m, H), 3.6~9.0 (b, 9H), 5.03 (s, 2H), 5.05 (s, 2H), 7.27 (s, 10H). IR (KBr) ν (cm$^{-1}$) = 3300, 2940, 1640, 1535, 1455, 1425, 1365, 1215, 1150, 1080, 1020, TLC (chloroform:methanol:17% aqueous ammonia = 6:2.5:0.5 v/v) Rf = 0.39. | NMR (D$_2$O, external TMS) δ = 1.6~3.1 (m, 14H), 3.3~4.1 (m, 12H), 4.5~4.9 (m, H). IR (KBr) ν (cm$^{-1}$) = 3290, 2940, 1640, 1540, 1450, 1365, 1260, 1225, 1165. |

| No. of compound | 10-{N-[4-(4-Guanidinophenyl)butyryl]-γ-amino-β-hydroxybutyryl}-1,5-dibenzyloxycarbonyl-1,5,10-triazadecane hydrochloride | 10-{N-[4-(4-Guanidinophenyl)butyryl]-γ-amino-β-hydroxybutyryl}-1,5,10-triazadecane trihydrochloride |
|---|---|---|
| 16 | NMR (CD$_3$OD) δ = 0.9~3.7 (m, 24H), 3.5~9.0 (b, 9H), 3.8~4.4 (m, H), 5.03 (s, 2H), 5.07 (s, 2H), 7.0~7.5 (m, 4H), 7.3 (s, 10H) IR (KBr) ν (cm$^{-1}$) = 3330, 2940, 1645, 1540, 1425, 1355, 1250, 1140, 1080. TLC (chloroform:methanol:17% aqueous ammonia = 6:1.5:0.25 v/v) Rf = 0.23 | NMR (D$_2$O, external TMS) δ = 1.7~3.3 (m, 14H), 3.3~4.0 (m, 10H), 4.3~4.8 (m, H), 7.6~8.0 (m, 4H) IR (KBr) ν (cm$^{-1}$) = 3290, 2940, 1630, 1545, 1515, 1440, 1255, 1170, 1085. |

| No. of compound | 10-{N-(6-Guanidinohexanoyl)-β-amino-α-hydroxypropanoyl}-1,5-dibenzyloxycarbonyl-1,5,10-triazadecane hydrochloride | 10-{N-(6-Guanidinohexanoyl)-β-amino-α-hydroxypropanoyl}-1,5,10-triazadecane trihydrochloride |
|---|---|---|
| 19 | NMR (CD$_3$OD) δ = 1.0~2.0 (m, 12H), 2.0~2.5 (m, 2H), 2.8~3.6 (m, 12H), 3.9~4.3 (m, H), 4.0~9.0 (b, 9H), 5.03 (s, 2H), 5.07 (s, 2H), 7.28 (s, 10H) IR (KBr) ν (cm$^{-1}$) = 3320, 2940, 2470, 1650, 1530, 1450, 1425, 1360, 1255, 1215, 1145, 1025. TLC (chloroform:methanol:17% aqueous ammonia = 6:2.5:0.5 v/v) | NMR (D$_2$O, external TMS) δ = 1.6~3.1 (m, 14H), 3.3~4.1 (m, 10H), 3.9~4.3 (d, 2H, J = 5 Hz, 4.6~5.0 (t, H, J = 5 Hz). IR (KBr) ν (cm$^{-1}$) = 3260, 2930, 2770, 2420, 2180, 1615, 1535, 1455, 1370, 1325, 1270, 1235, 1160. |

-continued

| No. of compound | 10-{N-(6-Guanidinohexanoyl)-β-amino-α-hydroxypropanoyl}-1,5-dibenzyloxy-carbonyl-1,5,10-triazadecane hydrochloride | 10-{N-(6-Guanidinohexanoyl)-β-amino-α-hydroxypropanoyl}-1,5,10-triazadecane trihydrochloride |
|---|---|---|
| | Rf = 0.56 | |

| No. of compound | 10-{N-(7-Guanidinoheptanoyl)-β-amino-α-hydroxypropanoyl}-1,5-dibenzyloxy-carbonyl-1,5,10-triazadecane hydrochloride | 10{N-(7-Guanidinoheptanoyl)-β-amino-α-hydroxypropanoyl}-1,5,10-triazadecane trihydrochloride |
|---|---|---|
| 22 | NMR (CD$_3$OD)<br>δ = 0.9~2.0 (m, 14H), 2.0~2.5 (m, 2H), 2.8~3.8 (m, 12H), 3.9~9.0 (b, 9H), 4.0~4.4 (t, H, J = 5 Hz), 5.03 (s, 2H), 5.07 (s, 2 H), 7.3 (s, 10H).<br>IR (KBr)<br>ν (cm$^{-1}$) = 3310, 2930, 2860, 1655, 1535, 1475, 1425, 1385, 1260, 1215, 1145, 1120, 1025.<br>TLC (chloroform:methanol:17% aqueous ammonia = 6:2.5:0.5 v/v)<br>Rf = 0.42. | NMR (D$_2$O, external TMS)<br>δ = 1.4~3.1 (m, 16H), 3.3~4.0 (m, 10H), 3.9~4.2 (d, 2H, J = 5 Hz), 4.6~5.0 (t, H, J = 5 Hz).<br><br>IR (KBr)<br>ν (cm$^{-1}$) = 3350, 2930, 1645, 1530, 1460, 1165, 1110. |

| No. of compound | 10-{N-(8-Guanidinooctanoyl)-β-amino-α-hydroxypropanoyl}-1,5-dibenzyloxy-carbonyl-1,5,10-triazadecane hydrochloride | 10{N-(8-Guanidinooctanoyl)-β-amino-α-hydroxypropanoyl}-1,5,10-triazadecane trihydrochloride |
|---|---|---|
| 25 | NMR (CD$_3$OD)<br>δ = 0.9~2.0 (m, 16H), 2.0~2.5 (m, 2H), 2.8~3.7 (m, 12H), 3.9~4.3 (m, H), 3.9~9.0 (b, 9H), 5.03 (s, 2H), 5.07 (s, 2H), 7.27 (s, 10H).<br>IR (KBr)<br>ν (cm$^{-1}$) = 3310, 2930, 2860, 1650, 1530, 1420, 1360, 1260, 1140.<br>TLC (chloroform:methanol:17% aqueous ammonia = 6:2.5:0.5 v/v)<br>Rf = 0.63. | NMR (D$_2$O, external TMS)<br>δ = 1.5~3.0 (m, 18H), 3.3~4.0 (m, 10H), 3.8~4.2 (d, 2H, J = 5 Hz), 4.6~5.0 (t, H, J = 5 Hz).<br><br>IR (KBr)<br>ν (cm$^{-1}$) = 3310, 2930, 1650, 1530, 1460, 1360, 1260, 1165, 1110. |

| No. of compound | 10-{N-[4-(4-Guanidinophenyl)butyryl]-β-amino-α-hydroxypropanoyl}-1,5-di-benzyloxycarbonyl-1,5,10-triazadecane hydrochloride | 10-{N-[4-(4-Guanidinophenyl)butyryl]-β-amino-α-hydroxypropanyl}-1,5,10-triazadecane trihydrochloride |
|---|---|---|
| 28 | NMR (CD$_3$OD)<br>δ = 0.9~3.7 (m, 22H) 3.5~9.0 (b, 9H), 3.9~4.3 (m, H), 5.03 (s, 2H), 5.07 (s, 2H), 7.0~7.5 (m, 4H), 7.3 (s, 10H)<br>IR (KBr)<br>ν (cm$^{-1}$) = 3300, 2930, 1660, 1510, 1425, 1255, 1140, 1020.<br>TLC (chloroform:methanol:17% aqueous ammonia = 6:1.5:0.25 v/v)<br>Rf = 0.2 | NMR (D$_2$O, external TMS)<br>δ = 1.7~3.3 (m, 12H), 3.3~4.0 (m, 8H), 3.8~4.1 (d, 2H, J = 5 Hz), 4.6~4.9 (t, H, J = 5 Hz), 7.5~8.0 (m, 4H).<br>IR (KBr)<br>ν (cm$^{-1}$) = 3320, 2950, 1640, 1535, 1440, 1250, 1110. |

We claim:
1. A novel spergualin-related compound represented by the general formula [I]:

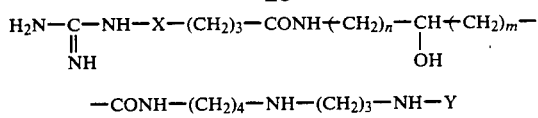

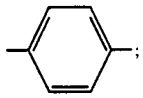

wherein X is -$(CH_2)_{15}$- or

Y is a hydrogen atom or a residue obtained by removing a hydroxyl group from the carboxyl group of an amino acid di or tripeptide; m and n are both 1, or a pharmacologically acceptable salt thereof.

2. A novel spergualin-related compound or a pharmacologically acceptable salt thereof as set forth in claim 1, wherein Y is a hydrogen atom.

3. A novel spergulain-related compound or a pharmacologically acceptable salt thereof as set forth in claim 1, wherein X is -$(CH_2)_{35}$-, Y is a hydrogen atom and m and n are each 1.

4. A novel spergualin-related compound represented by the formula:

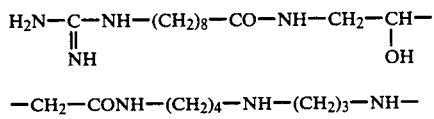

or a pharmacologically acceptable salt thereof.

5. A novel spergualin-related compound represented by the formula:

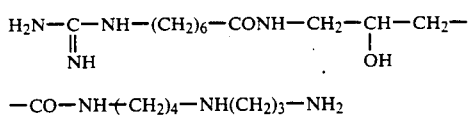

or a pharmacologically acceptable salt thereof.

6. An immunosuppressant containing a novel spergualin-related compound represented by the general formula [I]:

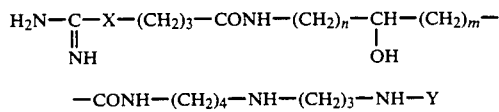

wherein X is -$(CH_2)_{15}$- or

Y is a hydrogen atom or a residue obtained by removing a hydroxyl group from the carboxyl group of an amino acid or di- or tri-peptide; m and n are both 1, or a pharmacologically acceptable salt thereof as an active ingredient.

* * * * *

UNITED STATES PATENT AND TRADEMARK OFFICE
CERTIFICATE OF CORRECTION

PATENT NO. : 5,061,787  Page 1 of 2
DATED : October 29, 1991
INVENTOR(S) : Tetsushi Saino, Tsugio Tomiyoshi, Kyuichi Nemoto and Yoshihisa Umeda It is certified that error appears in the above-identified patent and that said Letters Patent is hereby corrected as shown below:

On the title page:
Attorney, Agent, or Firm - "Nields & Lamack" should read --Nields & Lemack--

Column 8 line 40 "(m, 15H), 14.2" should read --(m, 15H), 1.42--

Column 13 line 7 "wherein X is $-(CH_2)_{15}-$ or" should read --wherein X is $-(CH_2)_{1-5}-$ or--

Column 13 line 23 "X is $-(CH_2)_{35}-$," should read --X is $-(CH_2)_{3-5}-$,--

UNITED STATES PATENT AND TRADEMARK OFFICE
CERTIFICATE OF CORRECTION

PATENT NO. : 5,061,787

DATED : October 29, 1991

INVENTOR(S) : Tetsushi Saino, Tsugio Tomiyoshi, Kyuichi Nemoto and Yoshihisa Umeda It is certified that error appears in the above-identified patent and that said Letters Patent is hereby corrected as shown below:

Column 14 line 21 "X is $-(CH_2)_{15}-$ or" should read --X is $-(CH_2)_{1-5}-$ or--

Signed and Sealed this

Second Day of February, 1993

*Attest:*

STEPHEN G. KUNIN

*Attesting Officer*   Acting Commissioner of Patents and Trademarks